US011805980B2

(12) United States Patent
Taniguchi et al.

(10) Patent No.: US 11,805,980 B2
(45) Date of Patent: Nov. 7, 2023

(54) IMAGING APPARATUS FOR ENDOSCOPE

(71) Applicant: Sony Olympus Medical Solutions Inc., Tokyo (JP)

(72) Inventors: Takuya Taniguchi, Tokyo (JP); Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 17/669,366

(22) Filed: Feb. 11, 2022

(65) Prior Publication Data
US 2022/0287548 A1   Sep. 15, 2022

(30) Foreign Application Priority Data

Mar. 15, 2021 (JP) ................. 2021-041206

(51) Int. Cl.
*H04N 23/50* (2023.01)
*A61B 1/00* (2006.01)

(52) U.S. Cl.
CPC ......... *A61B 1/00128* (2013.01); *H04N 23/50* (2023.01); *H04N 23/555* (2023.01)

(58) Field of Classification Search
CPC . A61B 1/00128; A61B 1/042; A61B 1/00195; H04N 23/50; H04N 23/555
See application file for complete search history.

(56) References Cited

U.S. PATENT DOCUMENTS

| 3,900,021 A * | 8/1975 | Makepeace ............. A61B 1/04 403/DIG. 1 |
| 5,836,867 A * | 11/1998 | Speier ................ G02B 23/2484 403/DIG. 1 |
| 6,805,665 B1 * | 10/2004 | Tatsuno ............. A61B 1/00188 600/101 |
| 2006/0229495 A1 * | 10/2006 | Frith .................. A61B 1/00126 600/112 |
| 2011/0193948 A1 * | 8/2011 | Amling ............. A61B 1/00029 348/E7.085 |
| 2015/0112141 A1 * | 4/2015 | Oginski ............. A61B 1/00112 600/136 |
| 2017/0318205 A1 * | 11/2017 | Duckett, III ............. A61B 1/07 |
| 2022/0192473 A1 * | 6/2022 | Deng ................. A61B 1/00197 |

FOREIGN PATENT DOCUMENTS

JP   2000-227559 A   8/2000

* cited by examiner

*Primary Examiner* — Michael Lee
(74) *Attorney, Agent, or Firm* — XSENSUS LLP

(57) ABSTRACT

An imaging apparatus for endoscope includes: a coupler configured to hold an endoscope for capturing an image of a subject, and emit the image of the subject; an imaging apparatus main body connected to the coupler so as to be relatively rotatable with respect to the coupler around an optical axis of the endoscope, the imaging apparatus main body being configured to capture the image of the subject emitted from the endoscope; and a posture keeping member configured to maintain a posture of the imaging apparatus main body with respect to the optical axis of the endoscope by generating a desired physical quantity between the coupler and the imaging apparatus main body.

10 Claims, 10 Drawing Sheets

IMAGING APPARATUS FOR ENDOSCOPE

This application claims priority from Japanese Application No. 2021-041206, filed on Mar. 15, 2021, the contents of which are incorporated by reference herein in its entirety.

BACKGROUND

The present disclosure relates to an imaging apparatus for endoscope.

In a medical field or an industrial field, an endoscope system that observes the inside of a subject such as a person or a mechanical structure is known (see, for example, JP 2000-227559 A).

An endoscope system described in JP 2000-227559 A includes an endoscope that captures and emits an image of a subject in a subject, and an imaging apparatus for endoscope that holds the endoscope and captures the image of the subject emitted from the endoscope.

Here, the imaging apparatus for endoscope includes a coupler and an imaging apparatus main body.

The coupler is a portion that holds the endoscope, and has a bottomed cylindrical shape to which an eyepiece of the endoscope is fitted.

The imaging apparatus main body is a portion that is connected to the coupler so as to be relatively rotatable about an optical axis of the endoscope and captures an image of a subject emitted from the endoscope.

That is, the coupler has a ring shape surrounding the optical axis of the endoscope, and has a coupler-side slide surface that slides with respect to the exterior casing of the imaging apparatus main body when rotating with respect to the imaging apparatus main body about the optical axis of the endoscope. On the other hand, the exterior casing of the imaging apparatus main body has a ring shape surrounding the optical axis of the endoscope, and has a casing-side slide surface that slides with respect to the coupler-side slide surface when rotating with respect to the coupler about the optical axis of the endoscope.

SUMMARY

FIGS. 9 and 10 are views for describing an issue in a known imaging apparatus 100 for endoscope. Note that in FIGS. 9 and 10, reference numeral "200" denotes the coupler described above. Further, the reference numeral "300" indicates the above-described imaging apparatus main body. Furthermore, a reference numeral "310" indicates an exterior casing of the imaging apparatus main body described above. Furthermore, the reference numeral "400" indicates the above-described endoscope. Furthermore, a reference numeral "Ax0" indicates an optical axis of the endoscope described above.

Meanwhile, in order to make the coupler 200 and the imaging apparatus main body 300 relatively rotatable about the optical axis Ax0 of the endoscope 400, it is necessary to provide a specific clearance between the coupler-side slide surface and the casing-side slide surface.

If a specific clearance is provided between the coupler-side slide surface and the casing-side slide surface as described above, the following problem occurs.

The state illustrated in FIG. 9 illustrates a state in which the separation distance between the coupler-side slide surface and the casing-side slide surface is constant over the entire circumference centered on the optical axis Ax0.

When the imaging apparatus 100 for endoscope is used, as illustrated in FIG. 10, the posture of the imaging apparatus main body 300 with respect to the optical axis Ax0 may be changed from the state illustrated in FIG. 9 by the own weight of the imaging apparatus main body 300. In this case, the coupler-side slide surface and the casing-side slide surface are in contact with each other at a portion on the vertical direction side (lower side) with respect to the optical axis Ax0, and are separated from each other at other portions. Therefore, in the above case, a load is applied to the portion on the vertical direction side between the coupler-side slide surface and the casing-side slide surface, and relative rotation of the coupler 200 and the imaging apparatus main body 300 about the optical axis Ax0 may not be smoothly performed.

According to one aspect of the present disclosure, there is provided an imaging apparatus for endoscope including: a coupler configured to hold an endoscope for capturing an image of a subject, and emit the image of the subject; an imaging apparatus main body connected to the coupler so as to be relatively rotatable with respect to the coupler around an optical axis of the endoscope, the imaging apparatus main body being configured to capture the image of the subject emitted from the endoscope; and a posture keeping member configured to maintain a posture of the imaging apparatus main body with respect to the optical axis of the endoscope by generating a desired physical quantity between the coupler and the imaging apparatus main body.

DETAILED DESCRIPTION

Figure 1:
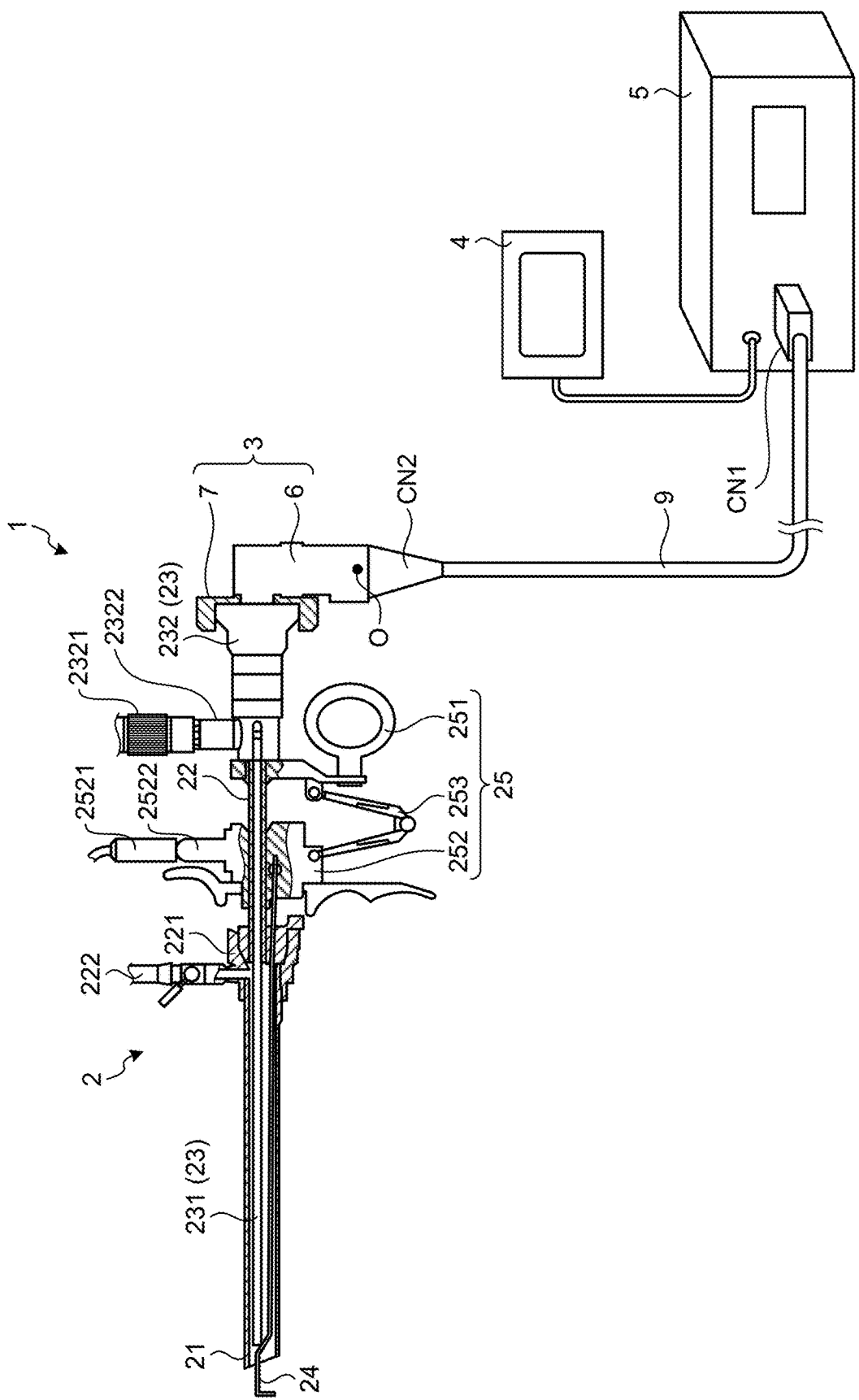
FIG. 1 is a view illustrating a configuration of an endoscope system according to a first embodiment.

Hereinafter, modes for carrying out the present disclosure (hereinafter, referred to as an embodiment) will be described with reference to the drawings. Note that the present disclosure is not limited by the embodiments described below. Furthermore, in the description of the drawings, the same portions are denoted by the same reference numerals.

First Embodiment

Schematic Configuration of Endoscope System

FIG. 1 is a view illustrating an endoscope system 1 according to a first embodiment.

An endoscope system 1 is used in the medical field, and is a device that treats (incises or the like) a living tissue while observing the inside of the living body. As illustrated in FIG.

1, the endoscope system 1 includes a resectoscope 2, an imaging apparatus 3 for endoscope, a display device 4, and a control device 5.

The resectoscope 2 is a portion that is inserted into a living body, captures an image of a subject, and treats a living tissue. As illustrated in FIG. 1, the resectoscope 2 includes a sheath 21, a guide tube 22, an endoscope 23, a resect electrode member 24, and a handle part 25.

The sheath 21 has a cylindrical shape and is a portion to be inserted into a living body.

The guide tube 22 has an outer diameter dimension smaller than the inner diameter dimension of the sheath 21, and is inserted into the sheath 21 from the proximal end side of the sheath 21 (right side in FIG. 1). Then, the distal end side of the guide tube 22 (left side in FIG. 1) is fixed to the proximal end side of the sheath 21 via a mounting member 221 (FIG. 1).

Here, the mounting member 221 is provided with a water supply port 222 for injecting liquid into the sheath 21 and supplying the liquid from a distal end of the sheath 21 (left end in FIG. 1).

The endoscope 23 is a portion that captures an image of a subject, and includes an insertion unit 231 and an eyepiece 232 as illustrated in FIG. 1.

The insertion unit 231 is fixed in the guide tube 22 and is inserted into the sheath 21. An optical system configured to use one or a plurality of lenses and condense light of an image of a subject is provided in the insertion unit 231.

The eyepiece 232 is connected to a proximal end of the insertion unit 231 (right end in FIG. 1). An eyepiece optical system (not illustrated) that emits an image of a subject collected by the optical system in the insertion unit 231 from the eyepiece 232 to the outside is provided in the eyepiece 232. The eyepiece 232 is formed in a tapered shape whose diameter is enlarged toward the side separated from the insertion unit 231 (right side in FIG. 1), and the imaging apparatus 3 for endoscope is detachably connected to the enlarged portion.

Here, as illustrated in FIG. 1, the eyepiece 232 is provided with a light source connector 2322 for connecting a light guide 2321. That is, the light supplied from the light source device (not illustrated) to the light guide 2321 is supplied to the insertion unit 231 via the eyepiece 232. The light supplied to the insertion unit 231 is emitted from the distal end of the insertion unit 231 (left end in FIG. 1) and emitted into the living body. The light emitted into the living body and reflected in the living body (the image of the subject) is taken into the insertion unit 231 from the distal end of the insertion unit 231 and emitted from the eyepiece 232 via the optical system (not illustrated) and the eyepiece optical system (not illustrated) in the insertion unit 231.

The resect electrode member 24 is inserted into the sheath 21 through the mounting member 221, and a distal end thereof (left end in FIG. 1) protrudes from the distal end of the sheath 21. Then, the distal end portion of the resect electrode member 24 comes into contact with the living tissue and treats the living tissue with a high-frequency current.

The handle part 25 is a portion where a doctor or the like grips the resectoscope 2 and operates the resect electrode member 24. As illustrated in FIG. 1, the handle part 25 includes a fixing ring 251, a slider 252, and a spring member 253.

The fixing ring 251 is a portion on which the doctor or the like hooks a thumb, and is fixed to the guide tube 22.

The slider 252 through which the guide tube 22 is inserted is configured to be movable in the left-right direction in FIG. 1 along the guide tube 22.

As illustrated in FIG. 1, the resect electrode member 24 is fixed to the slider 252. That is, the resect electrode member 24 moves toward and away in the left-right direction in FIG. 1 in the sheath 21 as the slider 252 moves.

In addition, a slider 252 is provided with a power supply connector 2522 for connecting a high frequency power supply cord 2521 that is connected to a high frequency power supply (not illustrated). The power supply connector 2522 is electrically connected to the resect electrode member 24 via a lead wire (not illustrated).

Further, as illustrated in FIG. 1, the slider 252 is provided with a finger hook member 2523 for the doctor or the like to hook a finger other than the thumb and move the slider 252 (move the resect electrode member 24 toward and away).

The spring member 253 has a substantially U shape, and has one end attached to the fixing ring 251 and the other end attached to the slider 252. The spring member 253 biases the slider 252 toward the side away from the fixing ring 251.

That is, the doctor or the like hooks the finger on the fixing ring 251 and the finger hook member 2523 and pulls the finger hook member 2523 against the biasing force of the spring member 253 to move the slider 252 to the right side in FIG. 1 (the resect electrode member 24 is moved to the right side in FIG. 1). On the other hand, when the doctor or the like releases the finger from the finger hook member 2523, the slider 252 (the resect electrode member 24) moves to the left side in FIG. 1 by the biasing force of the spring member 253.

The imaging apparatus 3 for endoscope is detachably connected to the eyepiece 232 of the resectoscope 2 (endoscope 23). Then, under the control of the control device 5, the imaging apparatus 3 for endoscope captures an image of a subject captured by the endoscope 23 (the image of the subject emitted from the eyepiece 232), and outputs an image signal obtained by the imaging (RAW signal).

Note that a detailed configuration of the imaging apparatus 3 for endoscope will be described in "Configuration of Imaging Apparatus for Endoscope" described later.

The display device 4 is configured using a display using liquid crystal, organic electro luminescence (EL), or the like. Then, the display device 4 displays an observation image or the like based on the video signal from the control device 5.

The control device 5 includes a central processing unit (CPU), a field-programmable gate array (FPGA), and the like, and integrally controls operations of the imaging apparatus 3 for endoscope, the display device 4, and a light source device (not illustrated). For example, the control device 5 performs predetermined image processing on the image signal (RAW signal) output from the imaging apparatus 3 for endoscope to generate a video signal for display. Then, the control device 5 causes the display device 4 to display the observation image based on the video signal. In addition, the control device 5 outputs a control signal, a synchronization signal, a clock, power, and the like to the imaging apparatus 3 for endoscope.

Configuration of Imaging Apparatus for Endoscope

Next, a detailed configuration of the imaging apparatus 3 for endoscope will be described.

Figure 2:
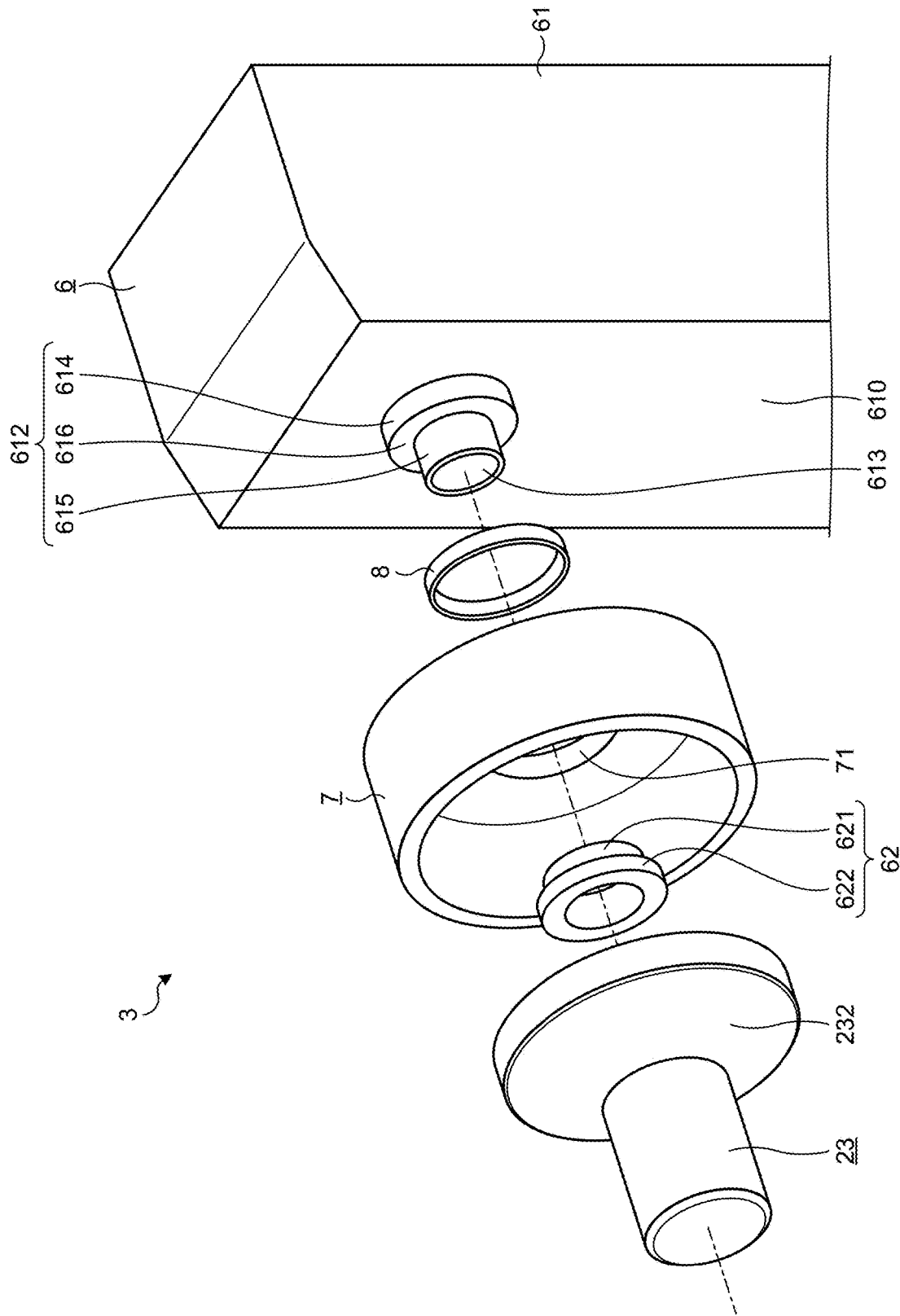
FIG. 2 is a view illustrating an imaging apparatus for endoscope.
Figure 3:
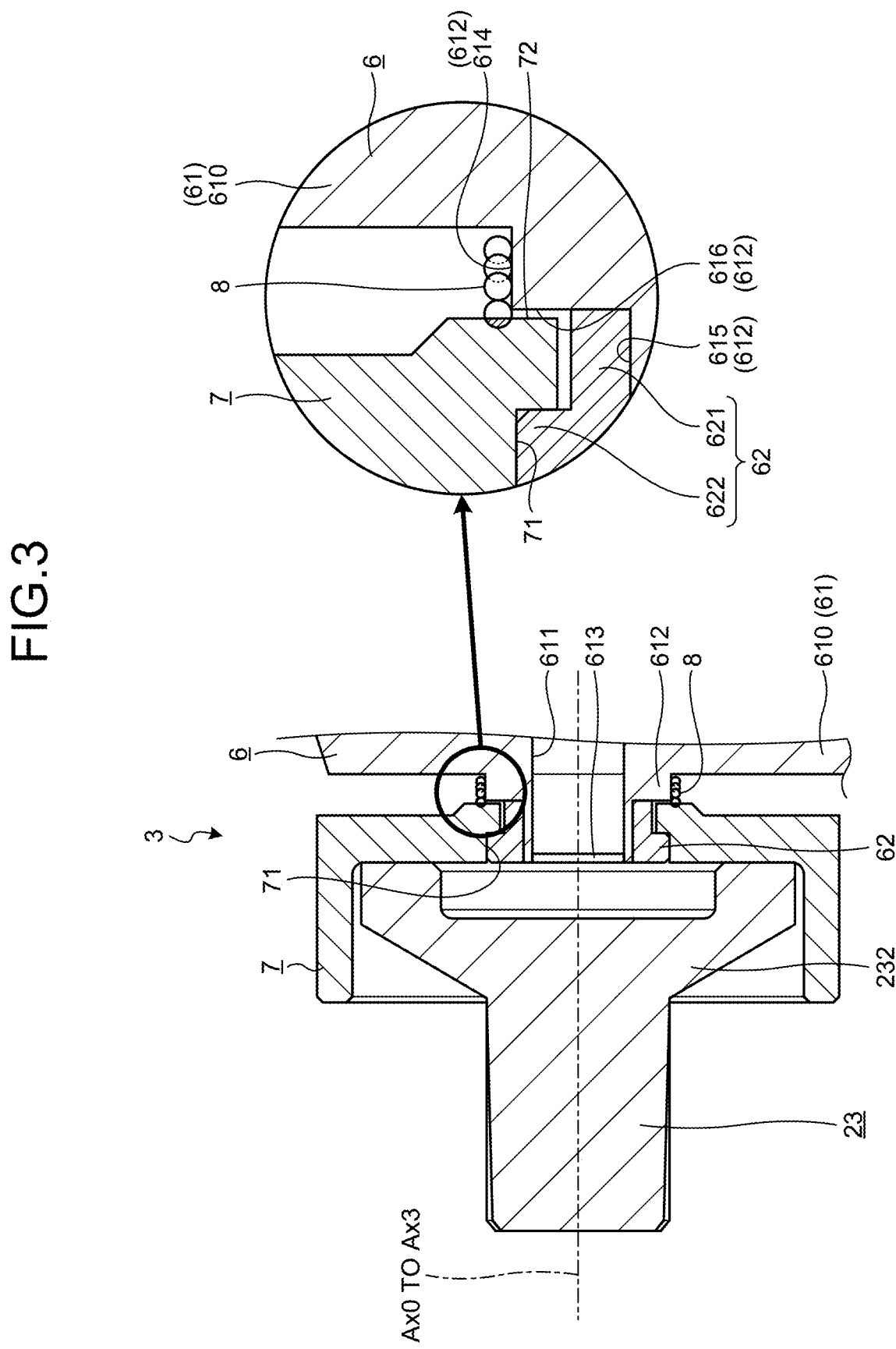
FIG. 3 is a view illustrating the imaging apparatus for endoscope.

FIGS. 2 and 3 are views illustrating the imaging apparatus 3 for endoscope. Specifically, FIG. 2 is an exploded perspective view of the imaging apparatus 3 for endoscope. FIG. 3 is a cross-sectional view of the imaging apparatus 3 for endoscope taken along a plane including the optical axis Ax0 of the endoscope 23. Note that, in FIGS. 2 and 3, the endoscope 23 is also illustrated for convenience of description.

As illustrated in FIGS. 1 to 3, the imaging apparatus 3 for endoscope includes an imaging apparatus main body 6, a coupler 7, a posture keeping member 8 (FIGS. 2 and 3), and a cable 9.

The imaging apparatus main body 6 is a portion that is connected to the coupler 7 so as to be relatively rotatable about an optical axis Ax0 of the endoscope 23 (FIGS. 2 and 3) and captures an image of a subject emitted from the endoscope 23. As illustrated in FIG. 2 or 3, the imaging apparatus main body 6 includes an exterior casing 61 and a mounting bush 62.

The exterior casing 61 is a casing that houses a lens unit (not illustrated) and an imaging unit (not illustrated) therein.

Here, the above-described lens unit forms an image of a subject emitted from the endoscope 23 on an imaging surface of the above-described imaging unit. In addition, the imaging unit described above includes an image sensor such as a charge coupled device (CCD) or a complementary metal oxide semiconductor (CMOS) that receives an image of a subject formed by the lens unit described above and converts the image of the subject into an electric signal under the control of the control device 5. Then, the imaging unit described above outputs an image signal obtained by imaging under the control of the control device 5.

As illustrated in FIG. 3, the exterior casing 61 is provided with a through hole 611 penetrating the inside and the outside of the exterior casing 61.

The through hole 611 is a circular hole provided in a portion located on the optical axis Ax0 of the endoscope 23 in a side wall 610 (FIGS. 2 and 3) of the exterior casing 61 facing the eyepiece 232 of the endoscope 23 in a state where the imaging apparatus 3 for endoscope is mounted on the eyepiece 232. Then, a central axis Ax1 (FIG. 3) of the through hole 611 substantially coincides with the optical axis Ax0 of the endoscope 23 in a state where the imaging apparatus 3 for endoscope is attached to the eyepiece 232 of the endoscope 23.

As illustrated in FIG. 2 or 3, the exterior casing 61 is provided with a protruding part 612.

The protruding part 612 has a substantially cylindrical shape protruding from a peripheral edge portion of the through hole 611 in the outer surface of the exterior casing 61 along the central axis Ax1 of the through hole 611. The inner diameter dimension of the protruding part 612 is the same as the inner diameter dimension of the through hole 611.

As illustrated in FIG. 2 or 3, an optical element 613 such as sapphire glass is fixed in the protruding part 612.

In addition, the outer surface of the protruding part 612 is formed in a stepped shape in which the proximal end side (right side in FIG. 3) is larger in outer diameter dimension than the distal end side (left side in FIG. 3). Hereinafter, for convenience of description, in the outer surface of the protruding part 612, a cylindrical surface having a large outer diameter dimension on the proximal end side is referred to as a large diameter surface 614, and a cylindrical surface having a small outer diameter dimension on the distal end side is referred to as a small diameter surface 615, and a stepped portion between the large diameter surface 614 and the small diameter surface 615 is referred to as a casing-side slide surface 616 (FIGS. 2 and 3).

Although not specifically illustrated, the small diameter surface 615 is provided with a screw groove.

The casing-side slide surface 616 has an annular shape centered on the central axis Ax1 of the through hole 611, and is formed of a flat surface orthogonal to the central axis Ax1.

The mounting bush 62 is a member for mounting the coupler 7 to the exterior casing 61. As illustrated in FIG. 2 or 3, the mounting bush 62 includes a bush main body 621 and a flange 622.

The bush main body 621 is formed in a cylindrical shape having an inner diameter dimension substantially the same as the outer diameter dimension of the small diameter surface 615 and having the outer diameter dimension smaller than the outer diameter dimension of the large diameter surface 614. Further, although not specifically illustrated, a screw groove is provided on the inner peripheral surface of the bush main body 621.

The flange 622 has an annular shape projecting from an end on the left side in FIG. 3 on the outer peripheral surface of the bush main body 621.

Then, the exterior casing 61 and the mounting bush 62 are fixed to each other by fastening a screw groove provided in the small diameter surface 615 and a screw groove provided in the inner peripheral surface of the bush main body 621. In this state, the central axis Ax2 (FIG. 3) of the bush main body 621 coincides with the central axis Ax1 of the through hole 611.

The coupler 7 is a portion that holds the endoscope 23, and has a bottomed cylindrical shape in which the eyepiece 232 may be fitted.

Although not specifically illustrated, a pressing part is provided on the inner peripheral surface of the coupler 7.

The pressing part described above is movable in a direction of approaching and separating from the central axis Ax3 (FIG. 3) of the coupler 7, has elasticity, and abuts on the outer peripheral surface of the eyepiece 232 fitted in the coupler 7 to press the eyepiece 232 toward the bottom portion of the coupler 7.

Then, in a state where the eyepiece 232 is fitted into the coupler 7, the optical axis Ax0 of the endoscope 23 coincides with the central axis Ax3 of the coupler 7.

In addition, a stepped through hole 71 having an inner surface shape substantially the same as the outer surface shape of the mounting bush 62 is provided in the bottom portion of the coupler 7, as illustrated in FIG. 2 or 3.

Hereinafter, for convenience of description, a peripheral edge portion of the through hole 71 on the outer surface of the coupler 7 will be referred to as a coupler-side slide surface 72. The coupler-side slide surface 72 has an annular shape centered on the central axis Ax3 of the coupler 7, and is formed of a flat surface orthogonal to the central axis Ax3.

The coupler 7 is attached to the imaging apparatus main body 6 as described below.

That is, with regard to the coupler 7, the operator inserts the protruding part 612 into the through hole 71 from the right side in FIG. 3 in a posture in which the opening having the bottomed cylindrical shape faces the left side in FIG. 3. Then, the operator fixes the mounting bush 62 to the exterior casing 61 as described above. Thus, the coupler 7 is attached to the imaging apparatus main body 6. In this state, the central axis Ax3 of the coupler 7 (the optical axis Ax0 of the endoscope 23) substantially coincides with the central axis Ax1 of the through hole 611. Further, as illustrated in FIG. 3, a specific clearance is provided between the casing-side slide surface 616 and the coupler-side slide surface 72. Then, the coupler 7 is rotatable about the optical axis Ax0 of the endoscope 23 with respect to the imaging apparatus main body 6.

Therefore, the imaging apparatus main body 6 is rotatable about the optical axis Ax0 of the endoscope 23 with respect to the eyepiece 232 of the endoscope 23 via the coupler 7. Furthermore, the imaging apparatus main body 6 is configured such that the center of gravity O (FIG. 1) is shifted from the central axis Ax1 of the through hole 611 (the optical axis Ax0 of the endoscope 23). Then, the imaging apparatus main body 6 is configured to rotate about the optical axis Ax0 regardless of the rotation of the endoscope 23 around the optical axis Ax0 in the resectoscope 2, and take a posture in which the center of gravity O is located below (on the vertical direction side) the optical axis Ax0.

The posture keeping member 8 is a member that maintains the posture of the imaging apparatus main body 6 with respect to the optical axis Ax0 of the endoscope 23. According to the first embodiment, the posture keeping member 8 is provided between the coupler 7 and the imaging apparatus main body 6, generates a desired physical quantity between the coupler 7 and the imaging apparatus main body 6 by abutting on the coupler 7 and the imaging apparatus main body 6, and maintains the posture of the imaging apparatus main body 6 with respect to the optical axis Ax0 of the endoscope 23. The posture keeping member 8 is formed of a coil spring which is an elastic member generating the physical quantity.

As illustrated in FIG. 3, the posture keeping member 8 is disposed at a position where the protruding part 612 is inserted, surrounds the large diameter surface 614, and faces the large diameter surface 614. In addition, one end of the posture keeping member 8 is in contact with the coupler-side slide surface 72 and the other end is in contact with the side wall 610 between the coupler-side slide surface 72 and the side wall 610 of the exterior casing 61. Then, the posture keeping member 8 maintains, by its elasticity, the posture of the imaging apparatus main body 6 with respect to the optical axis Ax0 of the endoscope 23. More specifically, the posture keeping member 8 maintains a state in which the central axis Ax1 of the through hole 611 coincides with the optical axis Ax0 of the endoscope 23 by its elasticity (corresponding to a physical quantity according to the present disclosure).

One end of the cable 9 is detachably connected to the control device 5 via the connector CN1 (FIG. 1), and the other end is detachably connected to the imaging apparatus main body 6 via the connector CN2 (FIG. 1). Then, the cable 9 transmits an image signal output from the imaging apparatus main body 6 to the control device 5, and transmits a control signal, a synchronization signal, a clock, power, and the like output from the control device 5 to the imaging apparatus main body 6.

According to the first embodiment described above, the following effects are obtained.

The imaging apparatus 3 for endoscope according to the first embodiment includes the posture keeping member 8 that is provided between the coupler 7 and the imaging apparatus main body 6, generates a desired physical quantity between the coupler 7 and the imaging apparatus main body 6 by abutting on the coupler 7 and the imaging apparatus main body 6, and maintains the posture of the imaging apparatus main body 6 with respect to the optical axis Ax0 of the endoscope 23.

Therefore, it is possible to avoid that the central axis Ax1 of the through hole 611 is inclined with respect to the optical axis Ax0 of the endoscope 23, and the coupler-side slide surface 72 and the casing-side slide surface 616 abut on each other at a portion on the vertical direction side with respect to the optical axis Ax0.

Therefore, according to the imaging apparatus 3 for endoscope of the first embodiment, without applying a load to the portion on the vertical direction side between the coupler-side slide surface 72 and the casing-side slide surface 616, it is possible to smoothly perform relative rotation of the coupler 7 and the imaging apparatus main body 6 about the optical axis Ax0 of the endoscope 23.

Further, in the imaging apparatus 3 for endoscope of the first embodiment, the posture keeping member 8 includes an elastic member.

Therefore, the posture keeping member 8 is elastically deformable at the time of relative rotation of the coupler 7 and the imaging apparatus main body 6 about the optical axis Ax0 of the endoscope 23. Therefore, it is possible to suppress the posture keeping member 8 from becoming a load in the relative rotation.

Furthermore, in the imaging apparatus 3 for endoscope according to the first embodiment, the posture keeping member 8 is configured by a coil spring, and is arranged at a position surrounding the large diameter surface 614 by the protruding part 612 being inserted.

Therefore, the posture keeping member 8 may be easily disposed, and the imaging apparatus 3 for endoscope may be easily assembled.

Second Embodiment

Next, a second embodiment will be described.

Hereinafter, the same reference numerals are given to the same configurations as those of the above-described first embodiment, and the detailed description thereof will be omitted or simplified.

Figure 4:
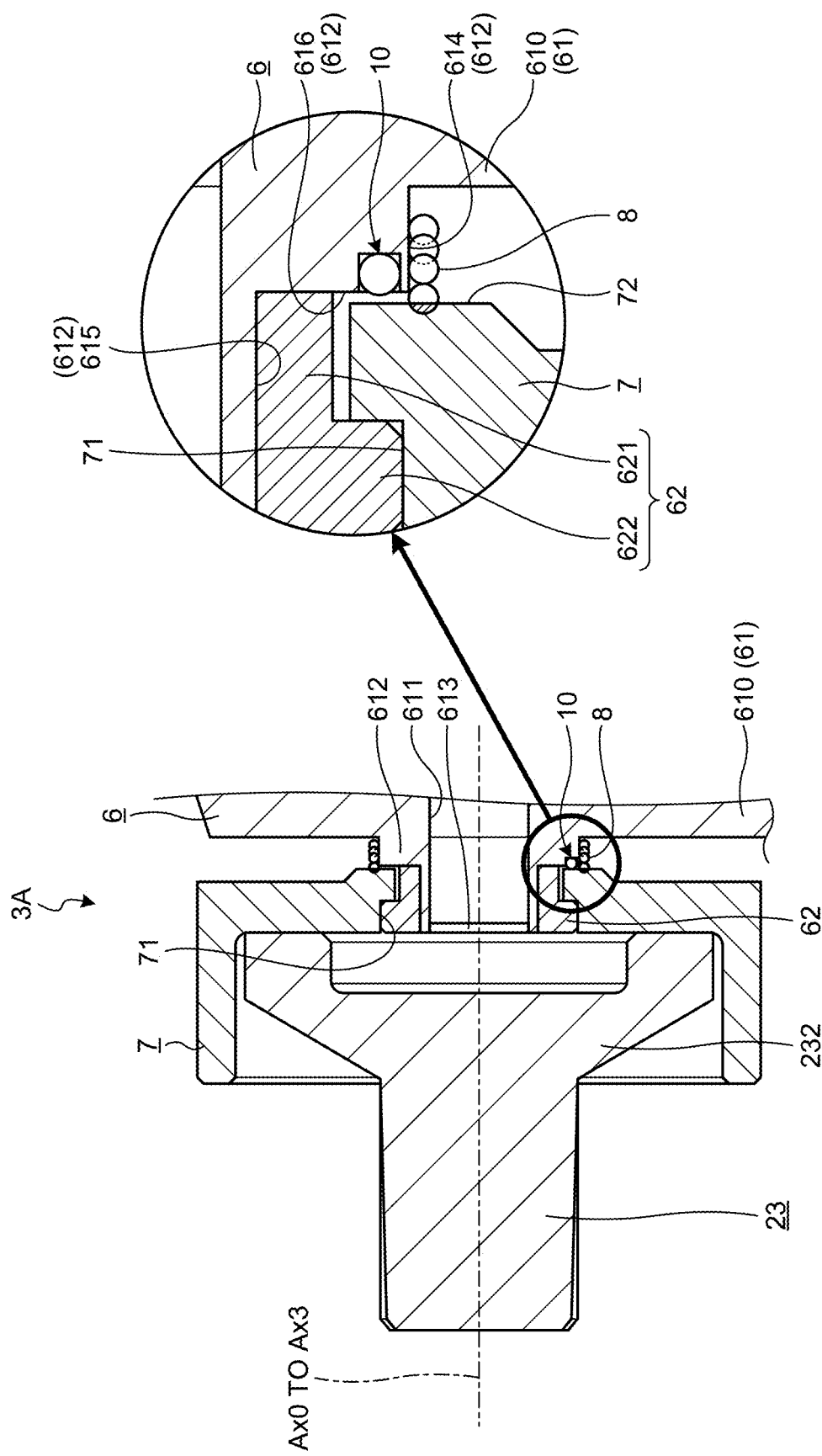
FIG. 4 is a view illustrating an imaging apparatus for endoscope according to a second embodiment.

FIG. 4 is a view illustrating an imaging apparatus 3A for endoscope according to the second embodiment. Specifically, FIG. 4 is a cross-sectional view corresponding to FIG. 3.

In the imaging apparatus 3A for endoscope according to the second embodiment, as illustrated in FIG. 4, a ball bearing 10 is provided in the imaging apparatus 3 for endoscope described in the above-described first embodiment.

The ball bearing 10 is provided, as illustrated in FIG. 4, with respect to the optical axis Ax0 of the endoscope 23, in the casing-side slide surface 616 on a side where the imaging apparatus main body 6 is close to the coupler 7 due to its own weight. In other words, the ball bearing 10 is provided on the casing-side slide surface 616 on the side (vertical direction side) where the center of gravity O of the imaging apparatus main body 6 is located by its own weight with respect to the optical axis Ax0 of the endoscope 23.

According to the second embodiment described above, the following effects are obtained in addition to the same effects as those of the first embodiment described above.

In the imaging apparatus 3A for endoscope according to the second embodiment, the ball bearing 10 is provided at the above-described position on the casing-side slide surface 616.

Therefore, even in the case where the central axis Ax1 of the through hole 611 is inclined with respect to the optical axis Ax0 of the endoscope 23 and the coupler-side slide surface 72 and the casing-side slide surface 616 are close to each other at a portion on the vertical direction side with respect to the optical axis Ax0, it is possible to make the coupler-side slide surface 72 abut on the ball bearing 10. That is, even in the case described above, the ball bearing 10 may reduce the load during the relative rotation of the coupler 7 and the imaging apparatus main body 6 about the optical axis Ax0 of the endoscope 23, and the rotation may be smoothly performed.

Note that in the above-described second embodiment, as for the ball bearing 10 on the casing-side slide surface 616, the configuration is not limited to the one where the center of gravity O of the imaging apparatus main body 6 is on the side located (vertical direction side) only by its own weight with respect to the optical axis Ax0 of the endoscope 23. The ball bearing 10 may be provided so as to constitute a part of an annular shape centered on the optical axis Ax0 of the endoscope 23 as long as the position on the vertical direction side is included.

The ball bearing 10 is not limited to be provided on the casing-side slide surface 616, and may be provided on the coupler-side slide surface 72. At this time, the ball bearing 10 is configured to have an annular shape centered on the optical axis Ax0 of the endoscope 23.

Furthermore, the ball bearing 10 described above may be adopted in the imaging apparatuses 3B to 3E for endoscope according to the following third to sixth embodiments.

Third Embodiment

Next, a third embodiment will be described.

Hereinafter, the same reference numerals are given to the same configurations as those of the above-described first embodiment, and the detailed description thereof will be omitted or simplified.

Figure 5:
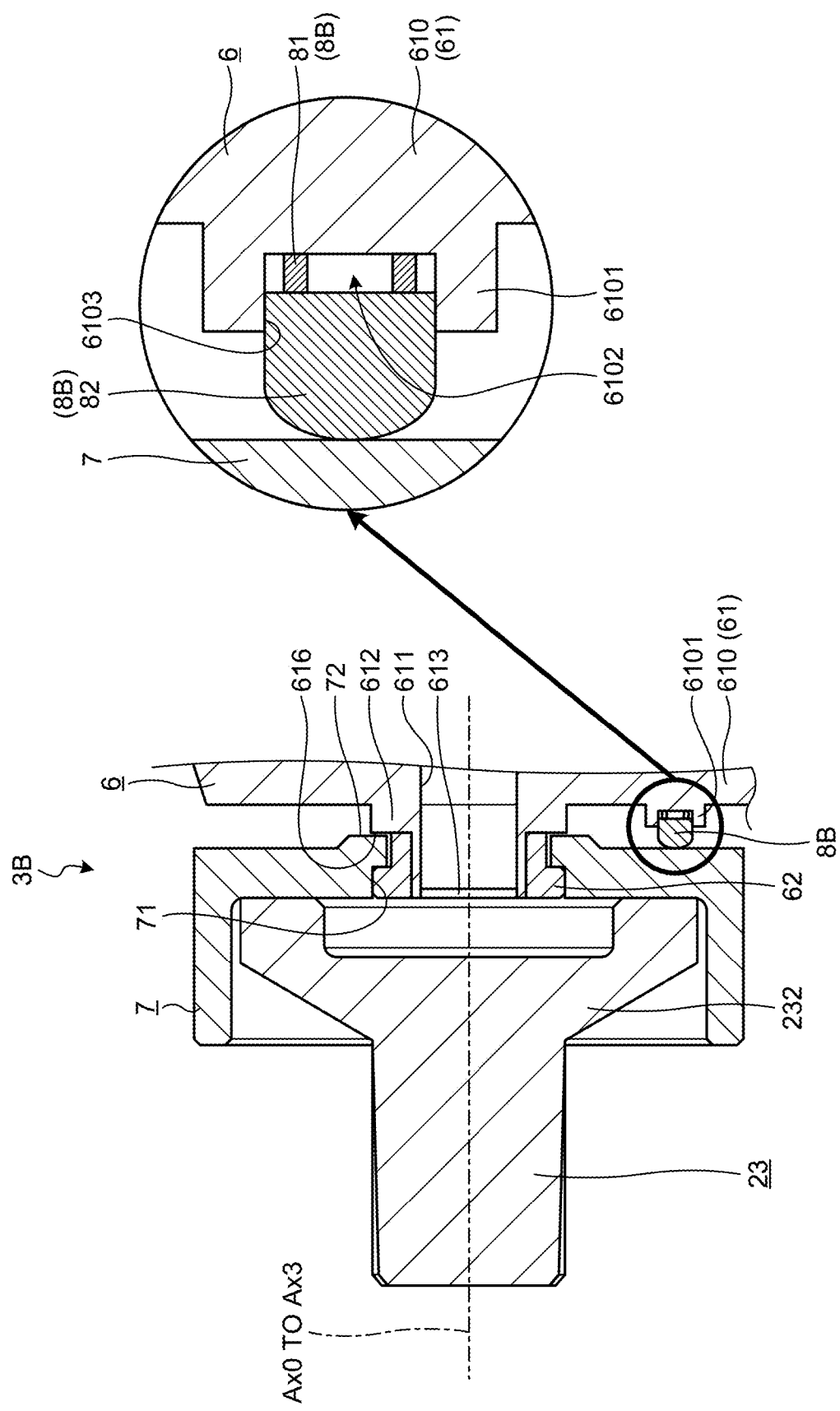
FIG. 5 is a view illustrating an imaging apparatus for endoscope according to a third embodiment.

FIG. 5 is a view illustrating an imaging apparatus 3B for endoscope according to the third embodiment. Specifically, FIG. 5 is a cross-sectional view corresponding to FIG. 3.

As illustrated in FIG. 5, in the imaging apparatus 3B for endoscope according to the third embodiment, a posture keeping member 8B having a configuration different from that of the posture keeping member 8 is adopted instead of the posture keeping member 8 with respect to the imaging apparatus 3 for endoscope described in the above-described first embodiment.

Here, as illustrated in FIG. 5, the side wall 610 according to the third embodiment is provided with a protruding part 6101 protruding along the central axis Ax1 of the through hole 611. More specifically, the protruding part 6101 is provided on the side wall 610 on the side where the imaging apparatus main body 6 is close to the coupler 7 by its own weight with respect to the optical axis Ax0 of the endoscope 23. In other words, the protruding part 6101 is provided on the side wall 610 on the side (vertical direction side) where the center of gravity O of the imaging apparatus main body 6 is located by its own weight with respect to the optical axis Ax0 of the endoscope 23.

As illustrated in FIG. 5, the protruding part 6101 is provided at its projecting end portion with a recess 6102 having an inner surface 6103 constituted by a cylindrical surface whose central axis is parallel to the central axis Ax1 of the through hole 611.

As illustrated in FIG. 5, the posture keeping member 8B includes an elastic member 81 and a contact member 82 as a configuration for generating a desired physical quantity between the coupler 7 and the imaging apparatus main body 6.

In the third embodiment, the elastic member 81 is formed of a coil spring. The elastic member 81 is disposed in the recess 6102, and one end (right end in FIG. 5) thereof is fixed to the bottom portion of the recess 6102.

The contact member 82 is a portion that is fixed to the other end (left end in FIG. 5) of the elastic member 81 disposed in the recess 6102 and abuts on the outer surface facing the protruding part 6101 in the coupler 7. The contact member 82 is made of a resin material, for example, and has a substantially cylindrical shape slightly smaller than the diameter of the inner surface 6103 of the recess 6102. In the contact member 82, a distal end portion (left end in FIG. 5) abutting on the coupler 7 is formed in a hemispherical shape as illustrated in FIG. 5. In addition, the contact member 82 is partly placed in the recess 6102 to be guided along the inner surface 6103 by the elasticity of the elastic member 81 and is placed so as to move toward and away from the coupler 7. That is, the posture keeping member 8B maintains a state in which the central axis Ax1 of the through hole 611 coincides with the optical axis Ax0 of the endoscope 23 when the contact member 82 presses the coupler 7 using the elasticity of the elastic member 81 (corresponding to a physical quantity according to the present disclosure).

According to the third embodiment described above, the following effects are obtained in addition to the same effects as those of the first embodiment described above.

In the imaging apparatus 3B for endoscope of the third embodiment, the posture keeping member 8B includes the above-described contact member 82 in addition to the elastic member 81.

Therefore, it is possible to reduce the contact area between the coupler 7 and the posture keeping member 8B, reduce the load during the relative rotation of the coupler 7 and the imaging apparatus main body 6 about the optical axis Ax0 of the endoscope 23, and the rotation may be further smoothly performed.

In particular, the contact member 82 is partly placed in the recess 6102 to be guided along the inner surface 6103 by the elasticity of the elastic member 81 and is placed so as to move toward and away from the coupler 7. Therefore, the function of "maintaining the posture of the imaging apparatus main body 6 with respect to the optical axis Ax0 of the endoscope 23" in the posture keeping member 8B may be favorably exhibited.

Note that the recess 6102 and the contact member 82 may be formed in an annular shape corresponding to the shape of the posture keeping member 8, and the recess 6102 and the contact member 82 may be adopted in the imaging apparatus 3 for endoscope described in the above-described first embodiment.

Fourth Embodiment

Next, a fourth embodiment will be described.

Hereinafter, the same reference numerals are given to the same configurations as those of the above-described first embodiment, and the detailed description thereof will be omitted or simplified.

Figure 6:
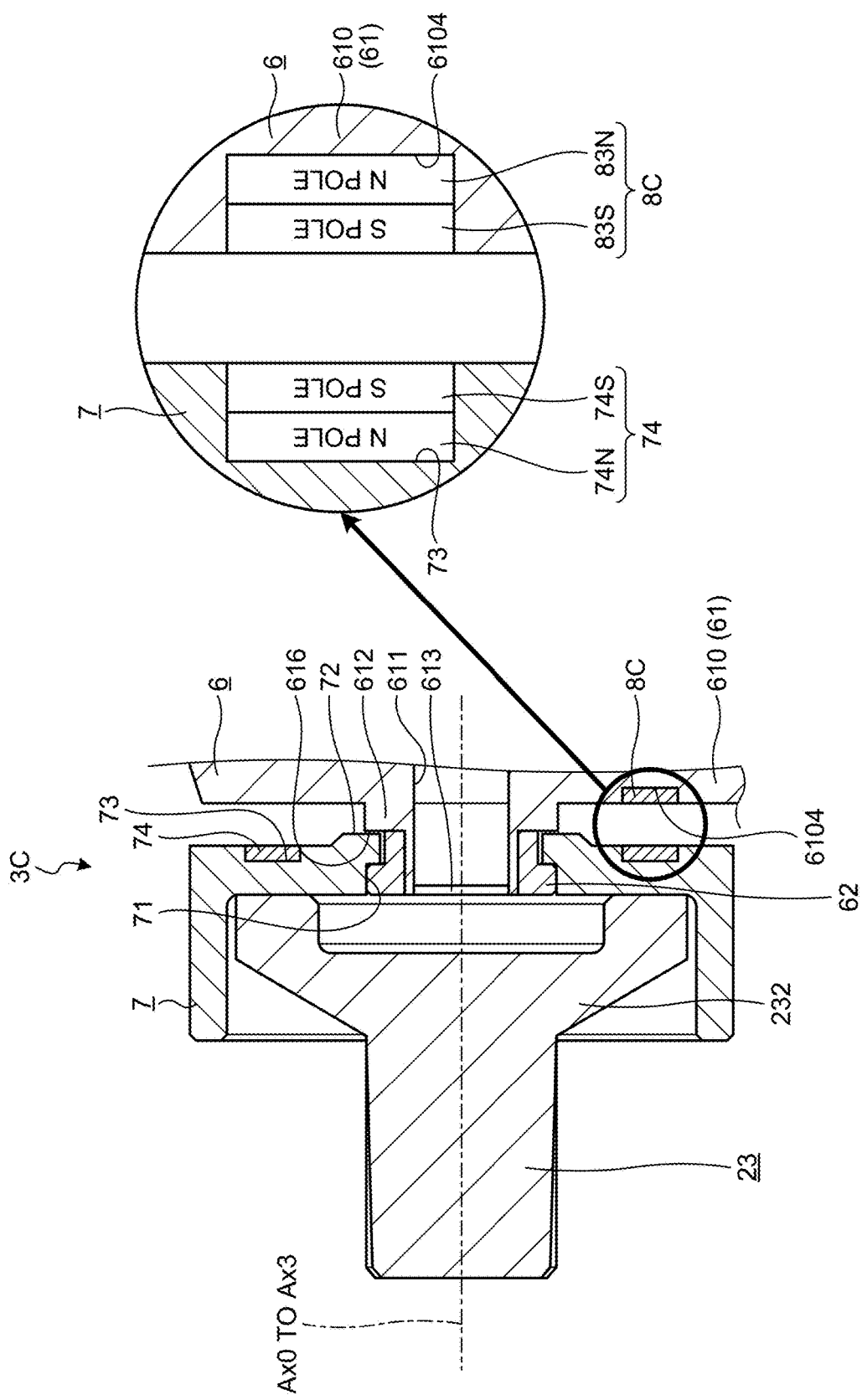
FIG. 6 is a view illustrating an imaging apparatus for endoscope according to a fourth embodiment.

FIG. 6 is a view illustrating an imaging apparatus 3C for endoscope according to the fourth embodiment. Specifically, FIG. 6 is a cross-sectional view corresponding to FIG. 3.

As illustrated in FIG. 6, in the imaging apparatus 3C for endoscope according to the fourth embodiment, a posture keeping member 8C having a configuration different from that of the posture keeping member 8 is adopted instead of the posture keeping member 8 with respect to the imaging apparatus 3 for endoscope described in the above-described first embodiment.

Here, in the coupler 7 according to the fourth embodiment, as illustrated in FIG. 6, an annular recess 73 centered on the central axis Ax3 of the coupler 7 is provided on a surface facing the side wall 610. An annular second permanent magnet 74 is fitted into the recess 73.

As illustrated in FIG. 6, the second permanent magnet 74 has a configuration in which an S pole 74S and an N pole 74N are arranged side by side along the central axis of the second permanent magnet 74. Then, the second permanent magnet 74 is fitted into the recess 73 in a state where the S pole 74S is exposed to the outside.

In the side wall 610 according to the fourth embodiment, as illustrated in FIG. 6, a recess 6104 is provided at a position facing the recess 73. More specifically, the recess 6104 is provided on the side wall 610 on the side where the imaging apparatus main body 6 is close to the coupler 7 by its own weight with respect to the optical axis Ax0 of the endoscope 23. In other words, the recess 6104 is provided on the side wall 610 on the side (vertical direction side) where the center of gravity O of the imaging apparatus main body 6 is located by its own weight with respect to the optical axis Ax0 of the endoscope 23.

The posture keeping member 8C includes a permanent magnet provided in the imaging apparatus main body 6 (corresponding to a first permanent magnet according to the present disclosure), and maintains the posture of the imaging apparatus main body 6 with respect to the optical axis Ax0 of the endoscope 23 by a magnetic force generated between the posture keeping member 8C and the second permanent magnet 74 provided in the coupler 7 (corresponding to a physical quantity according to the present disclosure).

Specifically, as illustrated in FIG. 6, the posture keeping member 8C is formed of a plate body in which an S pole 83S and an N pole 83N are arranged to be front and back, and is fitted into the recess 6104 in a state where the S pole 83S is exposed to the outside. Then, the posture keeping member 8C maintains a state in which the central axis Ax1 of the through hole 611 coincides with the optical axis Ax0 of the endoscope 23 by the repulsive force (magnetic force: corresponding to the physical quantity according to the present disclosure) acting between the posture keeping member 8C and the second permanent magnet 74.

According to the fourth embodiment described above, the following effects are obtained in addition to the same effects as those of the first embodiment described above.

In the imaging apparatus 3C for endoscope according to the fourth embodiment, the posture keeping member 8C maintains the posture of the imaging apparatus main body 6 with respect to the optical axis Ax0 of the endoscope 23 by the magnetic force generated between the posture keeping member 8C and the coupler 7 (the second permanent magnet 74).

Therefore, the posture keeping member 8C does not abut on the coupler 7. Therefore, the posture keeping member 8C does not become a load during the relative rotation of the coupler 7 and the imaging apparatus main body 6 about the optical axis Ax0 of the endoscope 23, and the rotation may be further smoothly performed.

In the fourth embodiment described above, the S pole and the N pole of the S pole 74S and the N pole 74N of the second permanent magnet 74 and the S pole 83S and the N pole 83N of the posture keeping member 8C may be arranged in reverse.

Fifth Embodiment

Next, a fifth embodiment will be described.

Hereinafter, the same reference numerals are given to the same configurations as those of the above-described fourth embodiment, and the detailed description thereof will be omitted or simplified.

Figure 7:
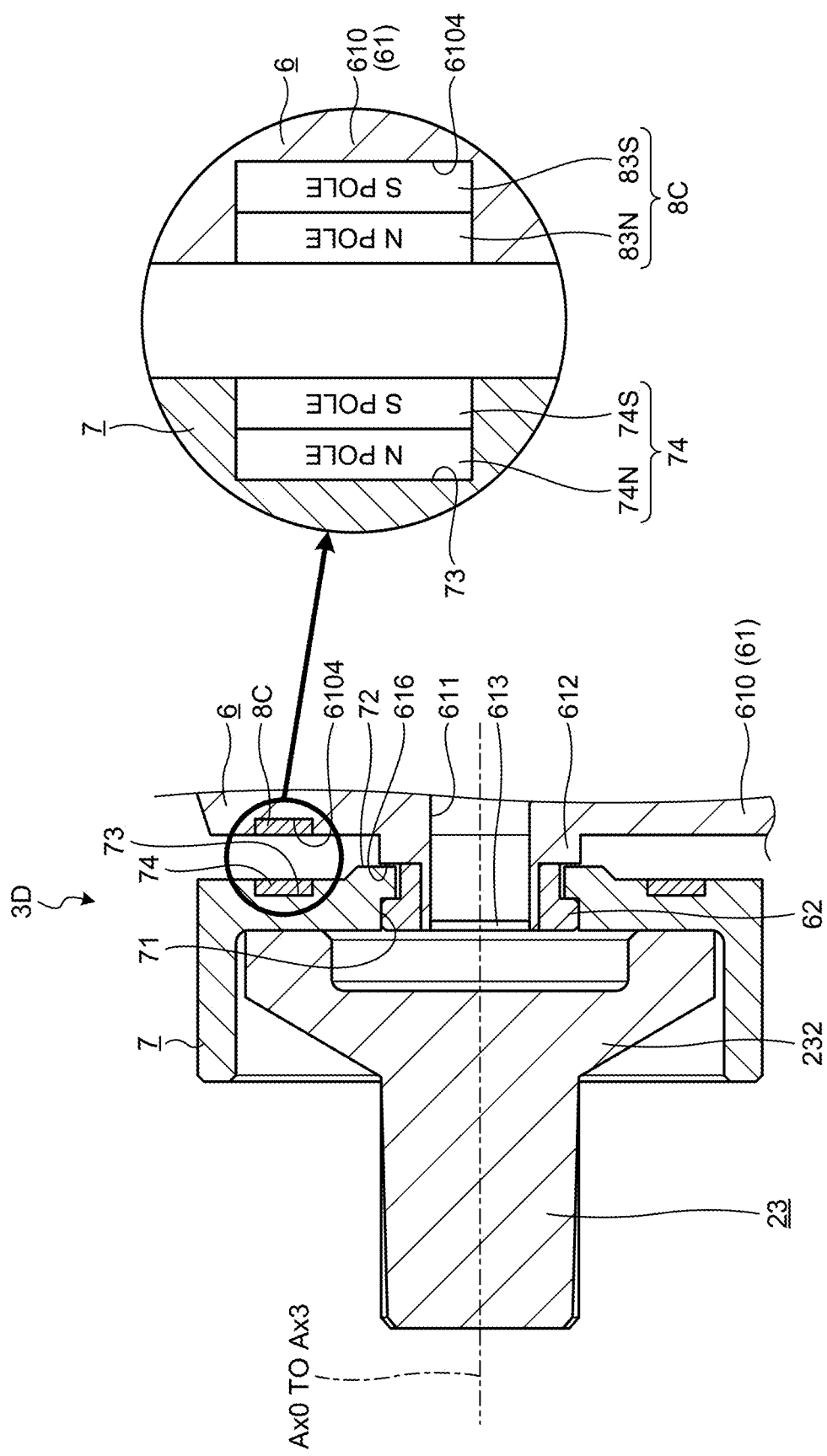
FIG. 7 is a view illustrating an imaging apparatus for endoscope according to a fifth embodiment.

FIG. 7 is a view illustrating an imaging apparatus 3D for endoscope according to the fifth embodiment. Specifically, FIG. 7 is a cross-sectional view corresponding to FIG. 6.

In the imaging apparatus 3D for endoscope according to the fifth embodiment, as illustrated in FIG. 7, the position where the recess 6104 is provided and the arrangement posture of the posture keeping member 8C are changed with respect to the imaging apparatus 3C for endoscope described in the above-described fourth embodiment.

The recess 6104 according to the fifth embodiment, as illustrated in FIG. 7, faces the recess 73 in the side wall 610, and is provided on a side where the imaging apparatus main body 6 is away from the coupler 7 due to its own weight with respect to the optical axis Ax0 of the endoscope 23. In other words, the recess 6104 faces the recess 73 and is provided on the side wall 610 on the side opposite (upper side) to the side (vertical direction side) where the center of gravity O of the imaging apparatus main body 6 is located by its own weight with respect to the optical axis Ax0 of the endoscope 23.

As illustrated in FIG. 7, the posture keeping member 8C according to the fifth embodiment is fitted into the recess 6104 in a state where the N pole 83N is exposed to the outside. Then, the posture keeping member 8C maintains a state in which the central axis Ax1 of the through hole 611 coincides with the optical axis Ax0 of the endoscope 23 by the gravitational force (magnetic force: corresponding to the physical quantity according to the present disclosure) acting between the posture keeping member 8C and the second permanent magnet 74.

Even when the position where the recess 6104 is provided and the arrangement posture of the posture keeping member 8C are changed as in the fifth embodiment described above, the same effects as those of the fourth embodiment described above are obtained.

In the fifth embodiment described above, the S pole and the N pole of the S pole 74S and the N pole 74N of the second permanent magnet 74 and the S pole 83S and the N pole 83N of the posture keeping member 8C may be arranged in reverse.

Sixth Embodiment

Next, a sixth embodiment will be described.

Hereinafter, the same reference numerals are given to the same configurations as those of the above-described fourth embodiment, and the detailed description thereof will be omitted or simplified.

Figure 8:
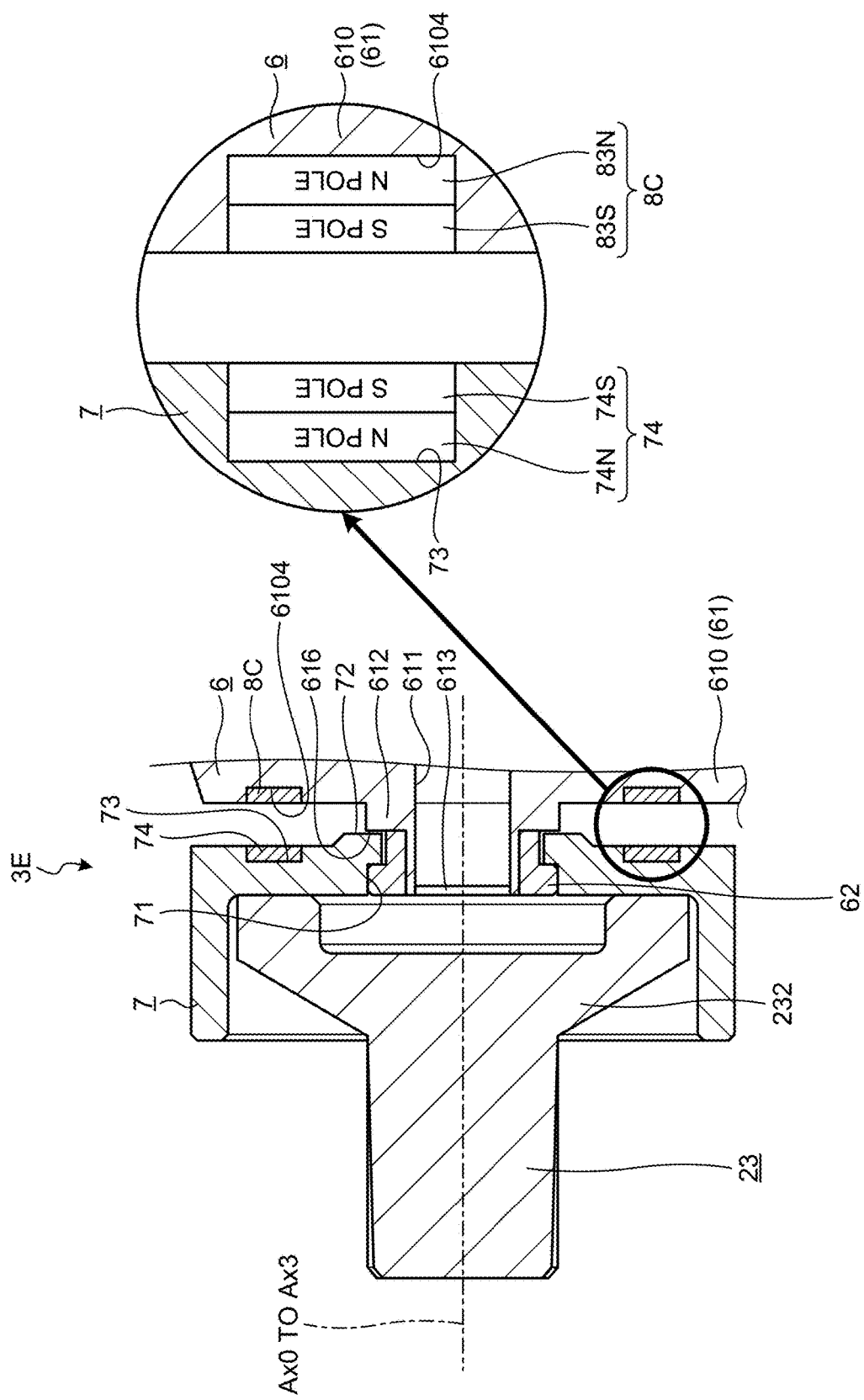
FIG. 8 is a view illustrating an imaging apparatus for endoscope according to a sixth embodiment.
Figure 9:
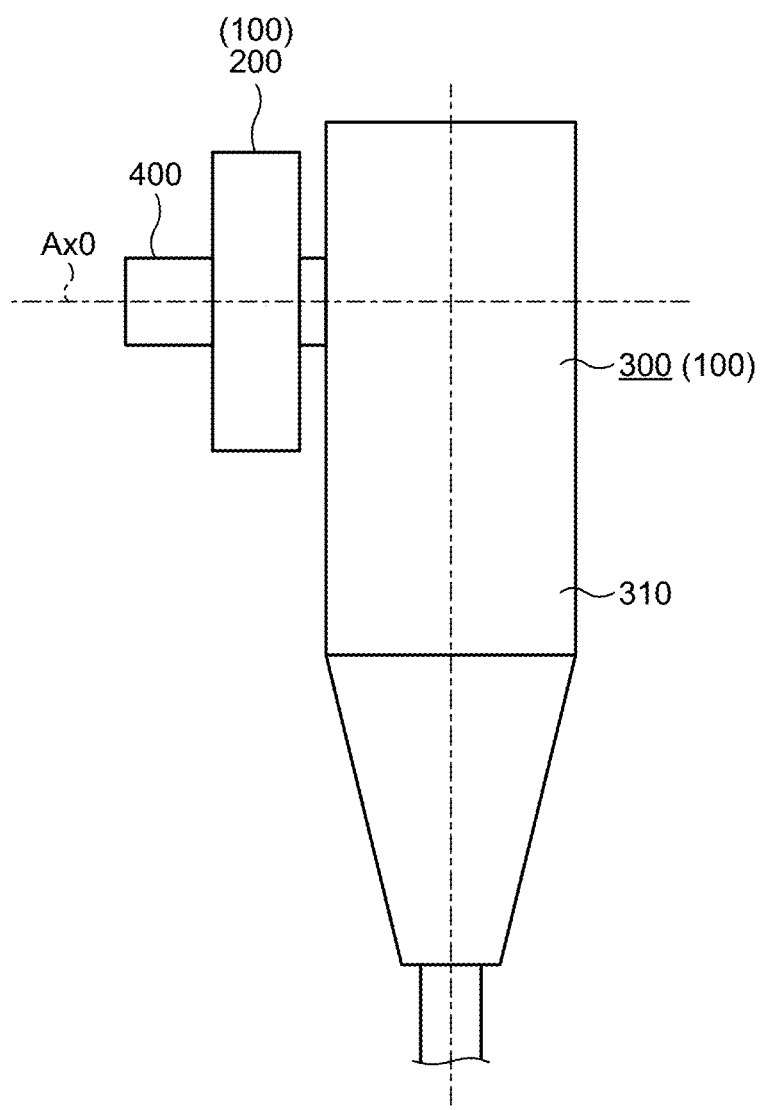
FIG. 9 is a view for describing a problem in a known imaging apparatus for endoscope.
Figure 10:
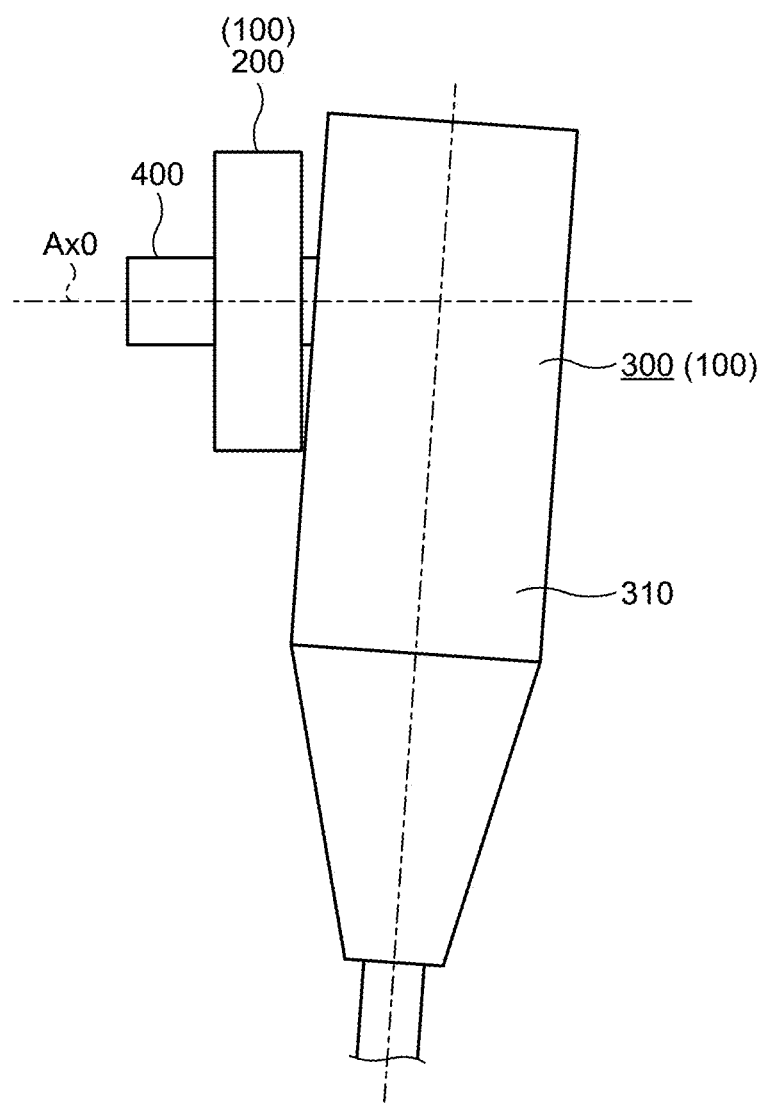
FIG. 10 is a view for describing a problem in a known imaging apparatus for endoscope.

FIG. 8 is a view illustrating an imaging apparatus 3E for endoscope according to the sixth embodiment. Specifically, FIG. 8 is a cross-sectional view corresponding to FIG. 6.

In the imaging apparatus 3E for endoscope according to the sixth embodiment, as illustrated in FIG. 8, the shapes of the recess 6104 and the posture keeping member 8C are changed with respect to the imaging apparatus 3C for endoscope described in the above-described fourth embodiment.

As illustrated in FIG. 8, the recess 6104 according to the sixth embodiment faces the recess 73 on the side wall 610 and has an annular shape centered on the central axis Ax1 of the through hole 611.

Similarly, as illustrated in FIG. 8, the posture keeping member 8C according to the sixth embodiment has an annular shape similar to the second permanent magnet 74, and is fitted into the recess 6104 in a state where the S pole 83S is exposed to the outside. Then, the posture keeping member 8C maintains a state in which the central axis Ax1 of the through hole 611 coincides with the optical axis Ax0 of the endoscope 23 by the repulsive force (magnetic force: corresponding to the physical quantity according to the present disclosure) acting between the posture keeping member 8C and the second permanent magnet 74.

Even when the shapes of the recess 6104 and the posture keeping member 8C are changed as in the sixth embodiment described above, the same effects as those of the fourth embodiment described above are obtained.

In the sixth embodiment described above, at least one of the S pole and the N pole of the S pole 74S and the N pole 74N of the second permanent magnet 74 and the S pole 83S and the N pole 83N of the posture keeping member 8C may be arranged in reverse.

Other Embodiments

Although the embodiments for carrying out the present disclosure have been described so far, the present disclosure should not be limited only by the first to sixth embodiments described above.

In the first to sixth embodiments described above, the case where the imaging apparatuses 3 and 3A to 3E for endoscope according to the present disclosure are used for the resectoscope 2 has been exemplified, but the present disclosure is not limited thereto, and the imaging apparatuses 3 and 3A to 3E for endoscope may be used for other various endoscopes (rigid endoscope and flexible endoscope).

In the above-described embodiments 1 to 3, the elastic member constituting the posture keeping members 8 and 8B that generate a desired physical quantity between the coupler 7 and the imaging apparatus main body 6 is not limited to the coil spring, and other members may be adopted as long as the members have elasticity.

Note that the following configurations also belong to the technical scope of the present disclosure.

(1) An imaging apparatus for endoscope including: a coupler configured to hold an endoscope for capturing an image of a subject, and emit the image of the subject; an imaging apparatus main body connected to the coupler so as to be relatively rotatable with respect to the coupler around an optical axis of the endoscope, the imaging apparatus main body being configured to capture the image of the subject emitted from the endoscope; and a posture keeping member configured to maintain a posture of the imaging apparatus main body with respect to the optical axis of the endoscope by generating a desired physical quantity between the coupler and the imaging apparatus main body.

(2) The imaging apparatus for endoscope according to (1), wherein the posture keeping member is provided between the coupler and the imaging apparatus main body, and the posture keeping member is configured to maintain the posture of the imaging apparatus main body with respect to the optical axis of the endoscope by generating the physical quantity while abutting on each of the coupler and the imaging apparatus main body.

(3) The imaging apparatus for endoscope according to (2), wherein the posture keeping member includes an elastic member.

(4) The imaging apparatus for endoscope according to (3), wherein the elastic member is a coil spring.

(5) The imaging apparatus for endoscope according to (3) or (4), wherein the elastic member has a ring shape that surrounds the optical axis of the endoscope.

(6) The imaging apparatus for endoscope according to any one of (3) to (5), wherein the posture keeping member includes a contact member fixed to an end, on the coupler side, of the elastic member, the contact member being configured to generate the physical quantity between the coupler and the imaging apparatus main body while abutting on the coupler.

(7) The imaging apparatus for endoscope according to (6), wherein the imaging apparatus main body includes an exterior casing including a recess facing the coupler, the elastic member is placed in the recess, and the contact member is partly placed in the recess to be guided along a side surface of the recess and is placed so as to move toward and away from the coupler.

(8) The imaging apparatus for endoscope according to (1), wherein the physical quantity includes a magnetic force, and the posture keeping member includes a first permanent magnet provided in the imaging apparatus main body, the posture keeping member being configured to maintain the posture of the imaging apparatus main body with respect to the optical axis of the endoscope by a magnetic force generated between the posture keeping member and the coupler.

(9) The imaging apparatus for endoscope according to (8), wherein the first permanent magnet is provided, with respect to the optical axis of the endoscope, on a side where the imaging apparatus main body is close to the coupler due to its own weight, the first member magnet being configured to maintain the posture of the imaging apparatus main body with respect to the optical axis of the endoscope by the magnetic force to repel the coupler.

(10) The imaging apparatus for endoscope according to (8), wherein the first permanent magnet is provided, with respect to the optical axis of the endoscope, on a side where the imaging apparatus main body is away from the coupler due to its own weight, the first member magnet being configured to maintain the posture of the imaging apparatus main body with respect to the optical axis of the endoscope by the magnetic force to attract the coupler.

(11) The imaging apparatus for endoscope according to (8), wherein the first permanent magnet has a ring shape that surrounds the optical axis of the endoscope.

(12) The imaging apparatus for endoscope according to any one of (8) to (11), wherein the coupler includes a second permanent magnet configured to generate the magnetic force to repel each other with the first permanent magnet or the magnetic force to attract each other with the first permanent magnet, and the second permanent magnet has a ring shape that surrounds the optical axis of the endoscope.

(13) The imaging apparatus for endoscope according to (1), wherein the coupler includes a coupler-side slide surface having a ring shape that surrounds the optical axis of the endoscope, the coupler-side slide surface being configured to slide with respect to an exterior casing of the imaging apparatus main body when the coupler rotates with respect to the imaging apparatus main body around the optical axis of the endoscope, the exterior casing of the imaging apparatus main body includes a casing-side slide surface having a ring shape that surrounds the optical axis of the endoscope, the casing-side slide surface being configured to slide with respect to the coupler-side slide surface when the exterior casing of the imaging apparatus main body rotates with respect to the coupler around the optical axis of the endoscope, and the imaging apparatus for endoscope further includes a ball bearing provided in one of the coupler-side slide surface and the casing-side slide surface.

(14) The imaging apparatus for endoscope according to (13), wherein the ball bearing is provided, with respect to the optical axis of the endoscope, in the casing-side slide surface on a side where the imaging apparatus main body is close to the coupler due to its own weight.

According to the imaging apparatus for endoscope of the present disclosure, it is possible to smoothly perform relative rotation of the coupler and the imaging apparatus main body about the optical axis of the endoscope.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An imaging apparatus for endoscope comprising:
    a coupler configured to hold an endoscope that captures and emits an image of a subject;
    an imaging apparatus main body connected to the coupler so as to be relatively rotatable with respect to the coupler around an optical axis of the endoscope, the imaging apparatus main body being configured to capture the image of the subject emitted from the endoscope; and
    a posture keeping member provided between the coupler and the imaging apparatus main body and configured to maintain a posture of the imaging apparatus main body with respect to the optical axis of the endoscope by generating a desired physical quantity between the coupler and the imaging apparatus main body while abutting on each of the coupler and the imaging apparatus main body, wherein
    the posture keeping member includes
        an elastic member; and
        a contact member fixed to an end, on the coupler side, of the elastic member, the contact member being configured to generate the desired physical quantity between the coupler and the imaging apparatus main body while abutting on the coupler, and wherein
    the imaging apparatus main body includes an exterior casing including a recess facing the coupler,
    the elastic member is placed in the recess, and
    the contact member is partly placed in the recess to be guided along a side surface of the recess, and is placed so as to move toward and away from the coupler.

2. The imaging apparatus for endoscope according to claim 1, wherein the elastic member is a coil spring.

3. The imaging apparatus for endoscope according to claim 1, wherein the elastic member has a ring shape that surrounds the optical axis of the endoscope.

4. An imaging apparatus for endoscope comprising:
    a coupler configured to hold an endoscope that captures and emits an image of a subject;
    an imaging apparatus main body connected to the coupler so as to be relatively rotatable with respect to the coupler around an optical axis of the endoscope, the imaging apparatus main body being configured to capture the image of the subject emitted from the endoscope; and
    a posture keeping member configured to maintain a posture of the imaging apparatus main body with respect to the optical axis of the endoscope by generating a desired physical quantity between the coupler and the imaging apparatus main body, wherein
    the desired physical quantity includes a magnetic force, and
    the posture keeping member includes a first permanent magnet provided in the imaging apparatus main body, the posture keeping member being configured to maintain the posture of the imaging apparatus main body with respect to the optical axis of the endoscope by a magnetic force generated between the posture keeping member and the coupler.

5. The imaging apparatus for endoscope according to claim 4, wherein the first permanent magnet is provided, with respect to the optical axis of the endoscope, on a side where the imaging apparatus main body is close to the coupler due to its own weight, the first permanent magnet being configured to maintain the posture of the imaging apparatus main body with respect to the optical axis of the endoscope by the magnetic force to repel the coupler.

6. The imaging apparatus for endoscope according to claim 4, wherein the first permanent magnet is provided, with respect to the optical axis of the endoscope, on a side where the imaging apparatus main body is away from the coupler due to its own weight, the first permanent magnet being configured to maintain the posture of the imaging apparatus main body with respect to the optical axis of the endoscope by the magnetic force to attract the coupler.

7. The imaging apparatus for endoscope according to claim 4, wherein the first permanent magnet has a ring shape that surrounds the optical axis of the endoscope.

8. The imaging apparatus for endoscope according to claim 4, wherein
    the coupler includes a second permanent magnet configured to generate the magnetic force to repel each other with the first permanent magnet or the magnetic force to attract each other with the first permanent magnet, and
    the second permanent magnet has a ring shape that surrounds the optical axis of the endoscope.

9. The imaging apparatus for endoscope according to claim 1, wherein
    the coupler includes a coupler-side slide surface having a ring shape that surrounds the optical axis of the endoscope, the coupler-side slide surface being configured to slide with respect to an exterior casing of the imaging apparatus main body when the coupler rotates with respect to the imaging apparatus main body around the optical axis of the endoscope,
    the exterior casing of the imaging apparatus main body includes a casing-side slide surface having a ring shape that surrounds the optical axis of the endoscope, the casing-side slide surface being configured to slide with respect to the coupler-side slide surface when the exterior casing of the imaging apparatus main body rotates with respect to the coupler around the optical axis of the endoscope, and
    the imaging apparatus for endoscope further comprises a ball bearing provided in one of the coupler-side slide surface and the casing-side slide surface.

10. The imaging apparatus for endoscope according to claim 9, wherein the ball bearing is provided, with respect to the optical axis of the endoscope, in the casing-side slide surface on a side where the imaging apparatus main body is close to the coupler due to its own weight.

* * * * *